(12) United States Patent
Yamamoto et al.

(10) Patent No.: US 11,007,358 B2
(45) Date of Patent: May 18, 2021

(54) MICRONEEDLE SHEET

(71) Applicant: HISAMITSU PHARMACEUTICAL CO., INC., Tosu (JP)

(72) Inventors: Naoki Yamamoto, Tsukuba (JP); Seiji Tokumoto, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 247 days.

(21) Appl. No.: 16/325,325

(22) PCT Filed: Aug. 30, 2017

(86) PCT No.: PCT/JP2017/031191
§ 371 (c)(1),
(2) Date: Feb. 13, 2019

(87) PCT Pub. No.: WO2018/043574
PCT Pub. Date: Mar. 8, 2018

(65) Prior Publication Data
US 2019/0201676 A1   Jul. 4, 2019

(30) Foreign Application Priority Data

Sep. 1, 2016   (JP) .............................. JP2016-170871

(51) Int. Cl.
*A61M 37/00* (2006.01)
*A61K 47/36* (2006.01)
*A61K 9/00* (2006.01)

(52) U.S. Cl.
CPC ............ *A61M 37/0015* (2013.01); *A61K 9/00* (2013.01); *A61K 47/36* (2013.01); *A61M 37/00* (2013.01);
(Continued)

(58) Field of Classification Search
CPC ...... A61M 37/0015; A61M 2037/0023; A61M 2037/0046
(Continued)

(56) References Cited

U.S. PATENT DOCUMENTS

2015/0157840 A1   6/2015   Kominami et al.
2015/0238743 A1   8/2015   Che et al.
(Continued)

FOREIGN PATENT DOCUMENTS

CN   104066475 A   9/2014
CN   102458359 B   1/2015
(Continued)

OTHER PUBLICATIONS

International Search Report dated Nov. 21, 2017 corresponding to application No. PCT/JP2017/031191.
(Continued)

*Primary Examiner* — Brandy S Lee
*Assistant Examiner* — Nidah M Hussain
(74) *Attorney, Agent, or Firm* — Nath, Goldberg & Meyer; Joshua B. Goldberg

(57) ABSTRACT

A microneedle sheet is disclosed that comprises a plurality of microneedles formed on a sheet generally along a principal surface of the sheet, wherein the microneedles contain a water-soluble polysaccharide and water, the water content is 1 mass % or more and less than 19 mass % based on the total mass of the microneedles, and the microneedles are raised from the principal surface by bending the sheet.

8 Claims, 1 Drawing Sheet

(52) U.S. Cl.
CPC ............... *A61M 2037/0023* (2013.01); *A61M 2037/0046* (2013.01); *A61M 2037/0053* (2013.01)

(58) Field of Classification Search
USPC ........................................................ 604/173
See application file for complete search history.

(56) References Cited

U.S. PATENT DOCUMENTS

| | | | |
|---|---|---|---|
| 2015/0374967 A1* | 12/2015 | Fudoji ............... | A61M 37/0015 604/173 |
| 2016/0279401 A1* | 9/2016 | Schwab ............ | A61M 37/0015 |
| 2017/0049695 A1 | 2/2017 | Yamamoto et al. | |

FOREIGN PATENT DOCUMENTS

| | | |
|---|---|---|
| CN | 104379209 A | 2/2015 |
| CN | 104780966 A | 7/2015 |
| CN | 205007427 U | 2/2016 |
| JP | 2005503210 A | 2/2005 |
| JP | 2015173901 A | 10/2015 |
| NO | 2012128363 A1 | 9/2012 |
| TW | 201545781 A | 12/2015 |
| WO | 03024518 A2 | 3/2003 |
| WO | 2013187392 A1 | 12/2013 |
| WO | 2014077243 A1 | 5/2014 |
| WO | 2014077244 A1 | 5/2014 |
| WO | 2015129545 A1 | 9/2015 |
| WO | 2016088886 A1 | 6/2016 |

OTHER PUBLICATIONS

International Preliminary Report on Patentability dated Mar. 14, 2019 corresponding to application No. PCT/JP2017/031191.
Chinese Office Action dated Sep. 1, 2020 corresponding to Patent Application No. 201780044994.9.
Office Action dated Dec. 18, 2019 corresponding to Taiwanese application No. 106129935.
Office Action dated Feb. 12, 2020 corresponding to Japanese application No. 2018-537352.
European Search Report dated Mar. 18, 2020 corresponding to application No. 17846578.7.
Office Action dated May 7, 2019 issued in corresponding Taiwanese Patent Application No. 106129935.
Korean Notice of Allowance dated Mar. 23, 2021 corresponding to patent application No. 10-2019-7000263.

* cited by examiner

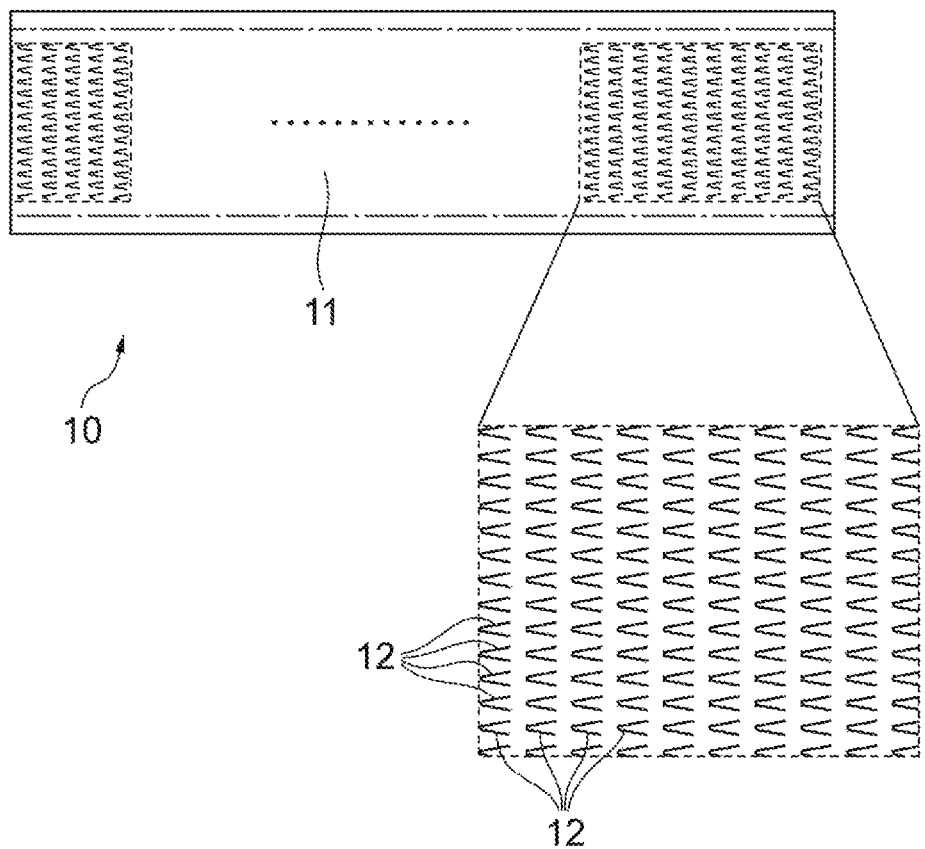

MICRONEEDLE SHEET

This is a National Phase Application filed under 35 U.S.C. 371 as a national stage of PCT/JP2017/031191, filed Aug. 30, 2017, an application claiming the benefit of Japanese Application No. 2016-170871, filed Sep. 1, 2016, the content of each of which is hereby incorporated by reference in its entirety.

TECHNICAL FIELD

One aspect of the present invention relates to a microneedle sheet for use to assist administration of an active component by a microneedle.

BACKGROUND ART

Conventionally, there have been known microneedles that administer active components through skin, and apparatuses comprising the microneedles. For example, a rotatable microstructure apparatus described in Patent Literature 1 below comprises a curved base substrate, and a roller structure including a plurality of microelements affixed upon a first surface of the base substrate. The plurality of microelements have a predetermined size and shape so as to penetrate through a stratum corneum layer of skin when the microstructure apparatus is placed upon the skin and rolled over the skin in a predetermined direction.

CITATION LIST

Patent Literature

Patent Literature 1: Japanese Unexamined Patent Publication No. 2005-503210
Patent Literature 2: International Publication No. WO2013/187392

SUMMARY OF INVENTION

Technical Problem

However, in the microstructure apparatus described in Patent Literature 1 above, since the microelements are exposed on the roller, there is a possibility that, before applying an active component to the skin through microneedles, the needles may touch or be caught on other objects (such as, for example, the user's skin and clothing). Therefore, there is a need for ensuring safety during handling of the microneedles.

In order to solve such a problem, in Patent Literature 2, there is proposed a microneedle sheet comprising a plurality of microneedles formed on a sheet generally along a principal surface of the sheet, in which the microneedles are raised from the principal surface by bending the sheet, and the raised microneedles pierce skin. In such a microneedle sheet, the microneedles are in a state of being generally along the principal surface of the sheet until the sheet is bent. This means that the tips of the microneedles do not protrude from the principal surface until the microneedles are applied to the skin. Therefore, unless the microneedle sheet is applied to the skin, there is no concern that the microneedles touch or be caught on other objects. As a result, the safety during handling of the microneedles can be ensured. Here, such a microneedle sheet is required to have bending resistance so that fracture, cracks, rupture or the like will not occur in the sheet even when the sheet is bent.

Solution to Problem

A microneedle sheet according to one aspect of the present invention comprises a plurality of microneedles formed on a sheet generally along a principal surface of a sheet. The microneedles comprise a water-soluble polysaccharide and water, the water content is 1 mass % or more and less than 19 mass % based on the total mass of the microneedles, and the microneedles are raised from the principal surface by bending the sheet. The raised microneedles pierce skin.

In this aspect, the sheet exhibits excellent bending resistance.

Advantageous Effects of Invention

According to the one aspect of the present invention, the safety during handling of the microneedles can be ensured and excellent bending resistance can be also exhibited.

BRIEF DESCRIPTION OF DRAWINGS

FIG. 1 is a plan view of a microneedle sheet according to an embodiment.

DESCRIPTION OF EMBODIMENTS

Embodiments of the present invention will be described in detail below with reference to the accompanying drawing.

The structure of a microneedle sheet 10 according to the embodiment will be described using FIG. 1. The microneedle sheet 10 is an instrument for administering any given active component (for example, drugs) into a living body, and includes a number of microneedles that pierce skin.

As shown in FIG. 1, the microneedle sheet 10 is in the form of a strip, and has a plurality of microneedles 12 formed on a sheet generally along a principal surface 11 of the sheet. The microneedles 12 are aligned in both the longitudinal direction and the width direction of the sheet, and the tips of the microneedles 12 are oriented to one end of the sheet (the left direction in FIG. 1). The tips of all the microneedles 12 may be oriented to one end of the sheet, or the tips of some microneedles 12 may be oriented to a direction different from the orientation of the other microneedles 12.

The microneedle sheet 10 and the microneedles 12 contain a water-soluble polysaccharide as a material and water, and the water content is 1 mass % or more and less than 19 mass % based on the total mass of the microneedles. By adopting such a material and setting the water content within the above range, it is possible to form a microneedle sheet having excellent bending resistance. In order to cause the microneedles to rise by bending the microneedle sheet and to pierce skin, the microneedle sheet needs to be bent sufficiently rather than a little. In other words, in order to realize such a function of the microneedle sheet, even if the curvature is large (the radius of curvature is small) when the microneedle sheet is bent, the microneedle sheet needs to withstand bending and be flexibly bent. Hence, the microneedle sheet with excellent bending resistance will keep strength and will not fracture, cracks or rupture even if the curvature is large when the microneedle sheet is bent.

The water-soluble polysaccharide is not particularly limited as long as it is a hydrophilic polysaccharide. The water-soluble polysaccharide can be a polysaccharide composed of one or more sugar units selected from the group consisting of aldoses, uronic acids, aldosamines, and derivatives thereof, specifically, for example, glycogen, carrageenan, agarose, amylose, amylopectin, xyloglucan, sodium hyaluronate, ethylcellulose, methylcellulose and hydroxyethylcellulose. From the viewpoint of bending resistance of the microneedle sheet, the water-soluble polysaccharide is preferably at least one water-soluble polysaccharide selected from the group consisting of sodium hyaluronate, sodium chondroitin sulfate, dextran, dextrin, carmellose sodium (carboxymethylcellulose sodium), chitosan, sodium alginate, and pullulan.

The lower limit of the water-soluble polysaccharide content is not particularly limited, and may be 60 mass %, 70 mass %, 81 mass %, 84 mass %, 87 mass % or 89 mass % based on the total mass of the microneedles 12. The upper limit of the water-soluble polysaccharide content is not particularly limited, and may be 95 mass %, 97 mass %, 98 mass %, 98.98 mass % or 99 mass % based on the total mass of the microneedles 12. As an example, the water-soluble polysaccharide content may be 81 mass % or more and 99 mass % or less, or 81.1 mass % or more and 98.98 mass % or less, based on the total mass of the microneedles 12. Since the microneedle sheet 10 is manufactured substantially uniformly as a whole, the water-soluble polysaccharide content based on the total mass of each individual microneedle 12 formed on the microneedle sheet 10 (that is, the total mass of one microneedle 12) is substantially the same as the water-soluble polysaccharide content based on the total mass of the sheet 10.

The water content is 1 mass % or more and less than 19 mass % based on the total mass of the microneedles 12. Since the microneedle sheet 10 is manufactured uniformly as a whole, the water content based on the total mass of each individual microneedle 12 formed on the microneedle sheet 10 (that is, the total mass of one microneedle 12) is substantially the same as the water content based on the total mass of the sheet 10. If the water content is less than 19 mass %, it is easy to form a microneedle sheet favorable for post-manufacture handling. The lower limit of the water content may be 2 mass %, 3 mass % or 5 mass % based on the total mass of the microneedles. The upper limit of the water content may be 16 mass %, 13 mass % or 11 mass % based on the total mass of the microneedles. Regarding a water content measurement method, the water content is measured according to a coulometric titration (Preparation 3) described in General Tests, "2.48 Water Determination (Karl Fischer Method)", in the Japanese Pharmacopoeia, Sixteenth Edition.

The microneedle sheet 10 and the microneedles 12 may further contain a plasticizer. The plasticizer is not particularly limited as long as it is a substance capable of imparting flexibility to the water-soluble polysaccharide, and, specific examples include fats and fatty oils, fatty acids or salts thereof, fatty acid esters, fatty alcohols, amine compounds, inorganic acids, organic acids, aromatic compounds, sugars, organic compounds and drugs. From the viewpoint of bending resistance of the microneedle sheet, the plasticizer may be selected from polyhydric alcohols, nonionic surfactants, inorganic acids, and organic acids.

The microneedles 12 can be formed by a laser or the like. The microneedles 12 can be formed by cutting the sheet with a laser. Since it is not necessary to raise the microneedles 12 from the principal surface 11 of the sheet in advance, the microneedle sheet 10 can be easily and inexpensively manufactured.

There is also no limitation on the dimensions of the microneedle sheet 10. Specifically, the lower limit of the thickness of the microneedle sheet 10 may be 5 µm, 10 µm, 20 µm or 25 µm, and the upper limit of the thickness may be 1000 µm, 300 µm, 200 µm, 180 µm, 150 µm, 100 µm or 90 µm. The lower limit of the thickness of the microneedle sheet 10 is determined considering the strength of the microneedles 12 that pierce skin, and the upper limit of the thickness is determined by considering the bendability of the sheet and the piercing characteristics of the microneedles 12. As an example, the thickness of the microneedle sheet 10 may be 10 to 300 µm inclusive, 10 to 200 µm inclusive, or 10 to 150 µm inclusive. The lower limit of the length of the microneedle sheet 10 may be 0.1 cm or 1 cm, and the upper limit of the length may be 50 cm or 20 cm. The lower limit of the width of the microneedle sheet 10 may be 0.1 cm or 1 cm, and the upper limit of the width may be 60 cm or 30 cm. The lower limits of the length and width of the microneedle sheet 10 are determined by considering the administration dose of the active component, and the upper limits of the length and width are determined considering the size of the living body.

There is also no limitation on parameters related to the microneedle 12. Specifically, the lower limit of the length of the microneedle 12 may be 10 µm or 100 µm, and the upper limit of the length may be 10000 µm or 1000 µm. Here, the length of the microneedle 12 is the distance from the bottom side (the root portion that is raised from the principal surface 11) of the microneedle 12 to the top portion. The lower limit of the density of the needles may be 0.05 needle/cm$^2$ or 1 needle/cm$^2$, and the upper limit of the density may be 10000 needles/cm$^2$ or 5000 needles/cm$^2$. The lower limit of the density is a value calculated from the number of and the area of the needles to which the active component can be administered, and the upper limit of the density is a limit value in consideration of the needle shape.

As shown in FIG. 1, in the present embodiment, each of the microneedles 12 has a triangular shape, but there is no limitation at all on the shape of the microneedle. Moreover, as shown in FIG. 1, in the present embodiment, the size and orientation of each of the microneedles 12 and the distribution in the microneedle sheet are uniform, but they are not necessarily uniform. When the microneedle 12 has a triangular shape, the angle of the tip portion of the microneedle 12 may be 10° or more, 20° or more, 150° or less, or 120° or less.

As a method for preparing the active component to be applied to skin, it is possible to consider a method in which the active component is included in the microneedle sheet 10 itself (in this case, the active component may be in a state of being dissolved or dispersed in the microneedle sheet), a method in which the microneedle sheet 10 itself is coated with the active component in advance, a method in which a layer containing the active component is added as an upper layer to the microneedle sheet 10 including the active component or to the microneedle sheet 10 which does not include the active component, a method in which the active component is applied to skin prior to piercing the skin with the microneedles 12, and a method in which the active component is applied to skin after piercing the skin with the microneedles 12. If the microneedle sheet 10 is coated with the active component in advance, a coating liquid having a predetermined viscosity is preferably applied to the entire sheet as uniformly as possible in thickness. Since the microneedles 12 are along the principal surface 11, such coating is easy. The coating may be performed using the principle of screen printing or other methods.

When applying the microneedle sheet 10 to the skin, an applicator can be used. It is possible to use a known applicator, for example, an applicator described in International Publication No WO2014/203911.

As described above, the microneedle sheet according to one aspect of the present invention comprises a plurality of microneedles formed on the sheet generally along the principal surface of the sheet. The microneedles comprise a water-soluble polysaccharide and water, the water content is 1 mass % or more and less than 19 mass % based on the total mass of the microneedles, the microneedles are raised from the principal surface by bending the sheet, and the raised microneedles pierce skin.

In this aspect, the microneedles are in a state of being generally along the principal surface of the sheet until the sheet is bent. This means that the tips of the microneedles do not protrude from the principal surface until the microneedles are applied to the skin. Therefore, unless the microneedle sheet is applied to the skin, there is no concern that the microneedles touch or be caught on other objects. As a result, the safety during handling of the microneedles can be ensured. For example, the user can safely store and transport the microneedle sheet and make preparations immediately before use.

Moreover, since one of the materials of the microneedles is a water-soluble polysaccharide, there is no need to purposely pull out the microneedles from the skin. Further, compared with a microneedle sheet of non-soluble material, the microneedle sheet made from a water-soluble polysaccharide material which is a soluble material is safer because physical irritation to the skin is less. Consequently, the convenience of the microneedle sheet is increased.

The water content is 1 mass % or more and less than 19 mass % based on the total mass of the microneedles. In addition to the inclusion of the above material, by setting the water content to 1 mass % or more and less than 19 mass % based on the total mass of the microneedles, the bending resistance of the microneedle sheet is improved.

In a microneedle sheet according to another aspect, the water-soluble polysaccharide may be a polysaccharide composed of one or more sugar units selected from the group consisting of aldoses, uronic acids, aldosamines, and derivatives thereof.

In a microneedle sheet according to other aspect, the water-soluble polysaccharide may be selected from sodium hyaluronate, sodium chondroitin sulfate, dextran, dextrin, carmellose sodium, chitosan, sodium alginate, and pullulan.

In a microneedle sheet according to other aspect, the thickness of the sheet may be 10 to 300 μm inclusive. By setting the thickness in such a range, the microneedle sheet is thin and flexible, and therefore the sheet can be applied to the skin in conformity to the shape of a living body, and consequently the active component can be efficiently administered. By using the water-soluble polysaccharide as a material of the microneedles, it is possible to prepare the microneedle sheet having solubility in the living body, and thinness which has never been achieved in the past.

Examples

Hereinafter, the present invention will be specifically described based on examples, but the present invention is not limited to the examples.

Microneedle sheets (1.0 cm×2.0 cm) were prepared using various materials. Specifically, each material and water were weighed, mixed and stirred in a container to completely dissolve the material, and the material was then defoamed centrifugally to prepare a coating solution. The solution was applied onto a liner and dried. Each polymer film prepared in this manner was subjected to laser processing to produce a microneedle sheet.

Pullulan, sodium hyaluronate, sodium chondroitin sulfate, carmellose sodium, or sodium alginate was used as a material.

For the prepared microneedle sheets, evaluation was conducted with respect to "formation into a sheet". Specifically, in the evaluation item "Formation into sheet" shown in Tables, an A mark indicates that a practical microneedle sheet (more specifically, a flat microneedle sheet) was prepared, and a B mark indicates that a sheet was not prepared because the solution was repelled from the liner and formed a lump, or other reason.

Additionally, for the prepared microneedle sheets, the water content was measured according to the coulometric titration (Preparation 3) described in General Tests, "2.48 Water Determination (Karl Fischer Method)", in the Japanese Pharmacopoeia, Sixteenth Edition. Each sample was heated to evaporate water, and nitrogen was introduced as a carrier into a titration flask.

After measuring the water content for each of the prepared microneedle sheets, a mandrel test (bending resistance test) was promptly conducted to evaluate the "bending resistance of sheet". A decrease in bending resistance is generally recognized in the sheets with microneedles formed thereon compared with sheets on which microneedles are not formed. IMC-A0F0 model of Imoto Machinery Co., Ltd. was employed as a bending test machine. Specifically, a mandrel (1 mm in diameter) of the bending test machine was set at the center of the microneedle sheet, and the microneedle sheet was bent together with the test machine. Then, by observing the bent microneedle sheet with a microscope, an evaluation was made as to whether or not there were fracture, cracks and rupture. An A mark in the Tables indicates that no fracture, cracks or rupture occurred, and a B mark indicates that fracture, cracks or rupture occurred. The capability of bending the microneedle sheet with the use of the mandrel having a diameter of 1 mm is preferable in order to exhibit the function as the microneedle sheet. The A marks in the Tables described later indicate the bending resistance of the microneedle sheets under the condition that the radius of curvature was 0.5 mm (that is, the curvature was large).

The results were summarized in Tables 1 to 5. The contents of material and water in the Tables indicate the mass % of material and water based on the total amount of the sheet after being dried. The thickness in the Tables is the thickness of the sheet after being dried.

As is clear from the results shown in the Tables, in any of the cases where water-soluble polysaccharides, such as pullulan, sodium hyaluronate, sodium chondroitin sulfate, carmellose sodium or sodium alginate, were used as materials, and when the water content ratio after dried was between 1.02 mass % and 18.90 mass %, microneedle sheets were able to be formed and the formed microneedle sheets were also excellent in bending resistance. On the other hand, even using any of the above water-soluble polysaccharides as a material, when the water content ratio was 0 mass %, microneedle sheets were able to be formed but the bending resistance of the formed microneedle sheets was poor.

TABLE 1

| | Composition | | | | | |
|---|---|---|---|---|---|---|
| | 1 | 2 | 3 | 4 | 5 | 6 |
| Pullulan | 84.33 | 89.88 | 90.32 | 91.22 | 95.22 | 96.98 |
| Water | 15.67 | 10.12 | 9.68 | 8.78 | 4.78 | 3.02 |
| Thickness (μm) | 50 | 80 | 25 | 180 | 25 | 180 |
| Formation into sheet | A | A | A | A | A | A |
| Bending resistance of sheet | A | A | A | A | A | A |

| | Composition | | | | |
|---|---|---|---|---|---|
| | 7 | 8 | 9 | 10 | 11 |
| Pullulan | 97.13 | 97.53 | 98.39 | 98.98 | 100.00 |
| Water | 2.87 | 2.47 | 1.61 | 1.02 | 0.00 |
| Thickness (μm) | 50 | 90 | 50 | 50 | 50 |
| Formation into sheet | A | A | A | A | A |
| Bending resistance of sheet | A | A | A | A | B |

TABLE 2

| | Composition | | | | | | |
|---|---|---|---|---|---|---|---|
| | 12 | 13 | 14 | 15 | 16 | 17 | 18 |
| Sodium hyaluronate | 81.59 | 84.81 | 87.31 | 94.73 | 95.52 | 96.65 | 100.00 |
| Water | 18.41 | 15.19 | 12.69 | 5.27 | 4.48 | 3.35 | 0.00 |
| Thickness (μm) | 50 | 25 | 70 | 50 | 50 | 50 | 50 |
| Formation into sheet | A | A | A | A | A | A | A |
| Bending resistance of sheet | A | A | A | A | A | A | B |

TABLE 3

| | Composition | | | | | |
|---|---|---|---|---|---|---|
| | 19 | 20 | 21 | 22 | 23 | 24 |
| Sodium chondroitin sulfate | 81.10 | 84.31 | 87.24 | 93.15 | 94.70 | 100.00 |
| Water | 18.90 | 15.69 | 12.76 | 6.85 | 5.30 | 0.00 |
| Thickness (μm) | 50 | 50 | 180 | 180 | 50 | 50 |
| Formation into sheet | A | A | A | A | A | A |
| Bending resistance of sheet | A | A | A | A | A | B |

TABLE 4

| | Composition | | | | | |
|---|---|---|---|---|---|---|
| | 25 | 26 | 27 | 28 | 29 | 30 |
| Carmellose sodium | 87.53 | 95.90 | 96.91 | 97.55 | 98.69 | 100.00 |
| Water | 12.47 | 4.10 | 3.09 | 2.45 | 1.31 | 0.00 |
| Thickness (μm) | 50 | 50 | 50 | 50 | 50 | 50 |
| Formation into sheet | A | A | A | A | A | A |
| Bending resistance of sheet | A | A | A | A | A | B |

TABLE 5

| Composition | 31 | 32 |
|---|---|---|
| Sodium alginate | 87.19 | 94.70 |
| Water | 12.81 | 5.30 |
| Thickness (μm) | 50 | 50 |
| Formation into sheet | A | A |
| Bending resistance of sheet | A | A |

REFERENCE SIGNS LIST

10 . . . microneedle sheet, 11 . . . principal surface, and 12 . . . microneedle.

The invention claimed is:

1. A microneedle sheet comprising a plurality of microneedles formed on a sheet generally along a principal surface of the sheet, wherein
   the microneedles comprise a water-soluble polysaccharide and water,
   a water content is 1 mass % or more and less than 19 mass % based on a total mass of the microneedles, and
   the microneedles are raised from the principal surface by bending the sheet.

2. The microneedle sheet according to claim 1, wherein the water-soluble polysaccharide is a polysaccharide composed of one or more sugar units selected from the group consisting of aldoses, uronic acids, aldosamines, and derivatives thereof.

3. The microneedle sheet according to claim 1, wherein the water-soluble polysaccharide is selected from sodium hyaluronate, sodium chondroitin sulfate, dextran, dextrin, carmellose sodium, chitosan, sodium alginate, and pullulan.

4. The microneedle sheet according to claim 1, wherein the sheet has a thickness of 10 to 300 μm inclusive.

5. The microneedle sheet according to claim 2, wherein the water-soluble polysaccharide is selected from sodium hyaluronate, sodium chondroitin sulfate, dextran, dextrin, carmellose sodium, chitosan, sodium alginate, and pullulan.

6. The microneedle sheet according to claim 2, wherein the sheet has a thickness of 10 to 300 μm inclusive.

7. The microneedle sheet according to claim 3, wherein the sheet has a thickness of 10 to 300 μm inclusive.

8. The microneedle sheet according to claim 5, wherein the sheet has a thickness of 10 to 300 μm inclusive.

* * * * *